US005756762A

United States Patent [19]
Kolb

[11] Patent Number: 5,756,762
[45] Date of Patent: May 26, 1998

[54] (S)-4-AMINO-HEPTA-5,6-DIENOIC ACID AND INTERMEDIATES THEROF

[75] Inventor: H. Michael Kolb, Cincinnati, Ohio

[73] Assignee: Merrell Pharmaceuticals Inc., Cincinnati, Ohio

[21] Appl. No.: 781,566

[22] Filed: Jan. 9, 1997

Related U.S. Application Data

[62] Division of Ser. No. 400,314, Mar. 6, 1995, Pat. No. 5,654,477, which is a continuation of Ser. No. 81,723, Jun. 23, 1993, abandoned.

[51] Int. Cl.$^6$ ................................................. C07D 207/46
[52] U.S. Cl. .................... 548/530; 548/545; 548/547; 548/551; 548/556; 548/574; 548/578
[58] Field of Search ............................ 548/530, 545, 548/547, 551, 556, 578, 574

[56] References Cited

FOREIGN PATENT DOCUMENTS 0492350  7/1992  European Pat. Off. .

OTHER PUBLICATIONS

Holmes et al. J. Chem. Soc. Perkin Trans., pp. 3301–3306, (1991).
Holmes et al. J. Chem. Soc. Perkin Trans., pp. 3307–3313, (1991).
Doedens, et al. J. Org. Chem. 53, 685–890, (1988).
Fischer, et al, Tetrahedron, vol. 42, No. 7, pp. 2063–2074, (1986).
Lindgren et al., Acta Pharm. Suec., vol. 12, No. 5–6, pp. 503–506, (1975).
"Allenic Amino Acids. 1. Synthesis of γ–Allenic GABA by a Novel Aza–Cope Rearrangement" A.L. Castelhano and A. Krantz, J. Amer. Chem. Soc. 1984, 106, pp. 1877–1879.

Primary Examiner—Johann Richter
Assistant Examiner—Jane C. Oswecki
Attorney, Agent, or Firm—David M. Stemerick

[57] ABSTRACT

The present invention relates to a novel enantiospecific processes for preparing (S)-4-amino-hepta-5,6-dienoic acid and pharmaceutically acceptable salts thereof, which is useful as an irreversible inhibitor of GABA-T, to novel intermediates thereof, and a process for preparing an intermediate thereof.

4 Claims, No Drawings

(S)-4-AMINO-HEPTA-5,6-DIENOIC ACID AND INTERMEDIATES THEROF

This is a division, of application Ser. No. 08/400,314, filed Mar. 6, 1995 now U.S. Pat. No. 5,654,477, which is a FWC of application Ser. No. 08/081,723, filed Jun. 23, 1993 now abandoned, which is herein incorporated by reference.

BACKGROUND OF THE INVENTION

The present invention relates to two novel processes or preparing (S)-4-amino-hepta-5,6-dienoic acid and pharmaceutically acceptable salts thereof, which are useful as irreversible inhibitors of GABA-T [U.S. Pat. No. 4,454,156, Jun. 12, 1984], to novel intermediates thereof, and a process for preparing an intermediate thereof.

The processes and intermediates of the present invention provide a novel enantiospecific method for preparing (S)-4-amino-hepta-5,6-dienoic acid.

SUMMARY OF THE INVENTION

The present invention provides two novel processes for preparing (S)-4-amino-hepta-5,6-dienoic acid and pharmaceutically acceptable salts thereof comprising the steps of:

(a) reacting a resolved amine of the formula:

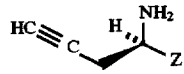
(1)

wherein
Z is $C_1$–$C_6$ alkyl, phenyl, or substituted phenyl bearing from 1 to 3 substituents chosen from the group consisting of $C_1$–$C_4$ alkyl, $C_1$–$C_4$ alkoxy, or halogen;
with an appropriate succinimide forming reagent to give a succinimide derivative;

(b) reacting a succinimide derivative with an appropriate reducing agent to give a 5'-hydroxybutyrolactam derivative;

(c) reacting a 5'-hydroxybutyrolactam derivative sequentially with an appropriate hydroxyl eliminating acid and an appropriate solvolysis agent to give (S)-5-propadienylbutyrolactam;

(d) reacting (S)-5-propadienylbutyrolactam with an appropriate lactam opening reagent to give (S)-4-amino-hepta-5,6-dienoic acid;

(e) optionally reacting (S)-4-amino-hepta-5,6-dienoic acid with an appropriate pharmaceutically acceptable acid or base to form a pharmaceutically acceptable salt thereof.

In addition, the present invention provides a novel process for preparing 5'-hydroxybutyrolactam derivatives of the formula:

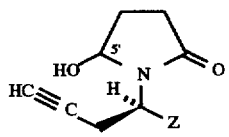
(3)

wherein
Z is $C_1$–$C_6$ alkyl, phenyl, or substituted phenyl bearing from 1 to 3 substituents chosen from the group consisting of $C_1$–$C_4$ alkyl, $C_1$–$C_4$ alkoxy, or halogen;

comprising the steps of:
(a) reacting a resolved amine of formula:

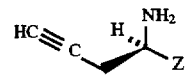
(1)

wherein
Z is $C_1$–$C_6$ alkyl, phenyl, or substituted phenyl bearing from 1 to 3 substituents chosen from the group consisting of $C_1$–$C_4$ alkyl, $C_1$–$C_4$ alkoxy, or halogen;
with an appropriate succinimide forming reagent to give a succinimide derivative.

(b) reacting a succinimide derivative with an appropriate reducing agent to give a 5'-hydroxybutyrolactam derivative.

In addition, the present invention provides a novel process for preparing (S)-4-amino-hepta-5,6-dienoic acid and pharmaceutically acceptable salts thereof comprising the steps of:

(a) reacting a 5'-hydroxybutyrolactam derivative of formula:

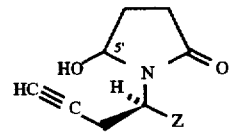
(3)

wherein
Z is $C_1$–$C_6$ alkyl, phenyl, or substituted phenyl bearing from 1 to 3 substituents chosen from the group consisting of $C_1$–$C_4$ alkyl, $C_1$–$C_4$ alkoxy, or halogen;
sequentially with an appropriate hydroxyl eliminating acid and an appropriate solvolysis agent to give (S)-5-propadienylbutyrolactam;

(b) reacting (S)-5-propadienylbutyrolactam with an appropriate lactam opening reagent to give (S)-4-amino-hepta-5,6-dienoic acid;

(c) optionally reacting (S)-4-amino-hepta-5,6-dienoic acid with an appropriate pharmaceutically acceptable acid or base to form a pharmaceutically acceptable salt thereof.

In addition, the present invention provides for novel succinimide derivatives of the formula:

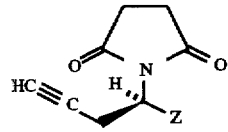

wherein
Z is $C_1$–$C_6$ alkyl, phenyl, or substituted phenyl bearing from 1 to 3 substituents chosen from the group consisting of $C_1$–$C_4$ alkyl, $C_1$–$C_4$ alkoxy, or halogen.

In addition, the present invention provides for novel 5'-hydroxybutyrolactam derivatives of the formula:

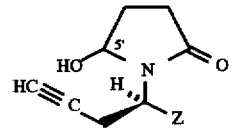

wherein
Z is $C_1$–$C_6$ alkyl, phenyl, or substituted phenyl bearing from 1 to 3 substituents chosen from the group consisting of $C_1$–$C_4$ alkyl, $C_1$–$C_4$ alkoxy, or halogen.

DETAILED DESCRIPTION OF THE INVENTION

As used in this application:

a) the term "$C_1$–$C_6$ alkyl" refers to a branched or straight chained, or cyclic alkyl radical containing from 1–6 carbon atoms, such as methyl, ethyl, n-propyl, isopropyl, n-butyl, isobutyl, t-butyl, n-pentyl, cyclopentyl, n-hexyl, cyclohexyl, and the like;

b) the term "$C_1$–$C_6$ alkyl" refers to a branched or straight chained alkyl radical containing from 1–4 carbon atoms, such as methyl, ethyl, n-propyl, isopropyl, n-butyl, isobutyl, t-butyl, and the like;

c) the term "$C_1$–$C_6$ alkoxy" refers to a branched or straight chained alkoxy radical containing from 1–4 carbon atoms, such as methoxy, ethoxy, n-propoxy, isopropoxy, n-butoxy, isobutoxy, t-butoxy, and the like;

d) the term "halogen" refers to a fluorine atom, a chlorine atom, a bromine atom, or an iodine atom;

e) the term "substituted phenyl" refers to;

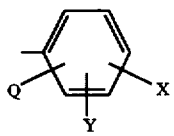

wherein

Q, Y, and X are independently chosen from the group consisting of; hydrogen, $C_1$–$C_4$ alkyl, $C_1$–$C_4$ alkoxy, or halogen;

f) the designation "▬" refers to a bond that protrudes forward out of the plane of the page.

g) The designation "▬" refers to a bond that protrudes backward out of the plane of the page.

h) the designation "∿" refers to a bond for which the stereochemistry is not designated.

i) the term "lower alkanol" refers to alcohols containing from 1 to 4 carbon atoms, specifically included in the term are methanol, ethanol, 1-propanol, 2-propanol, 1-butanol, and 2-butanol.

j) the term "pharmaceutically acceptable salts" refers to either acid addition salts or to base addition salts.

The expression "pharmaceutically acceptable acid addition salts" is intended to apply to any non-toxic organic or inorganic acid addition salt of (S)-4-amino-hepta-5,6-dienoic acid or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, and sulfonic acids such as p-toluenesulfonic acid, methane sulfonic acid and 2-hydroxyethane sulfonic acid. Such salts can exist in either a hydrated or substantially anhydrous form.

The expression "pharmaceutically acceptable basic addition salts" is intended to apply to any non-toxic organic or inorganic basic addition salts of (S)-4-amino-hepta-5,6-dienoic acid or any of its intermediates. Illustrative bases which form suitable salts include alkali metal or alkaline-earth metal hydroxides such as sodium, potassium, calcium, magnesium, or barium hydroxides; ammonia, and aliphatic, cyclic, or aromatic organic amines such as methylamine, dimethylamine, trimethylamine, triethylamine, diethylamine, isopropyldiethylamine, pyridine and picoline.

As is well known by one of ordinary skill in the art the Cahn-Ingold-Prelog designation of (R)- and (S)- for the stereochemistry of compounds of formula (1), (2), and (3) depends on the nature of Z.

For purposes of this application, the N-substituted-butyrolactam derivatives wherein there may be ambiguity as to which positions the numbers designate, numbers referring to the positions on the N-substituted-butyrolactam ring will bear a "'" and numbers referring to positions other than on the N-substituted-butyrolactam ring will not bear a "'".

Examples of compounds encompassed by the present invention include:

(R)-N-(1-Phenyl-but-3-yne)succinimide;

(R)-N-[1-(4-Chlorophenyl)-but-3-yne]succinimide;

(R)-N-[1-(4-Bromophenyl)-but-3-yne]succinimide;

(R)-N-[1-(4-Methylphenyl)-but-3-yne]succinimide;

(R)-N-[1-(4-Methoxyphenyl)-but-3-yne]succinimide;

(R)-N-[1(2,4-Dimethylphenyl)-but-3-yne]succinimide;

(R)-N-[1-(2,4,6-Trimethylphenyl)-but-3-yne]succinimide;

(S)-N-(1-Ethyl-but-3-yne)succinimide;

(S)-N-(1-Propyl-but-3-yne)succinimide;

(R)-N-(1-t-Butyl-but-3-yne)succinimide;

(R)-N-(1-Cyclohexyl-but-3-yne)succinimide;

(1R,5'R and 1R,5'S)-N-(1-Phenyl-but-3-yne)-5'-hydroxybutyrolactam;

(1R,5'R and 1R,5'S)-N-[1-(4-Chlorophenyl)-but-3-yne]-5'-hydroxybutyrolactam;

(1R,5'R and 1R,5'S)-N-[1-(4-Bromophenyl)-but-3-yne]-5'-hydroxybutyrolactam;

(1R,5'R and 1R,5'S)-N-[1-(4-Methylphenyl)-but-3-yne]-5'-hydroxybutyrolactam;

(1R,5'R and 1R,5'S)-N-[1-(4-Methoxyphenyl)-but-3-yne]-5'-hydroxybutyrolactam;

(1R,5'R and 1R,5'S)-N-[1-(2,4-Dimethylphenyl)-but-3-yne]-5'-hydroxybutyrolactam;

(1R,5'R and 1R,5'S)-N-[1-(2,4,6-Trimethylphenyl)-but-3-yne ]5'-hydroxybutyrolactam;

(1S,5'R and 1S,5'S)-N-(1-Ethyl-but-3-yne)-5'-hydroxybutyrolactam;

(1S,5'R and 1S,5'S)-N-(1-Propyl-but-3-yne)-5'-hydroxybutyrolactam;

(1R,5'R and 1R,5'S)-N-(1-t-Butyl-but-3-yne)-5'-hydroxybutyrolactam;

(1R,5'R and 1R,5'S)-N-(1-Cyclohexyl-but-3-yne)-5'-hydroxybutyrolactam.

As is appreciated by one of ordinary skill in the art the methodology disclosed in this application can be used to prepare either of the enantiomers of 4-amino-hepta-5,6-dienoic acid and either of the enantiomers of the succinimide derivatives herein disclosed, and all the diastereomers of the 5'-hydroxybutyrolactam derivatives herein disclosed. The enantiomer of 4-amino-hepta-5,6-dienoic acid that is produced depends on the stereochemistry of the starting material.

A general synthetic procedure for preparing (S)-4-amino-hepta-5,6-dienoic acid is set forth in Scheme A. In Scheme A, all substituents unless otherwise indicated, are as previously defined. Starting materials, reagents, techniques, and procedures used in Scheme A are well known and appreciated by one of ordinary skill in the art.

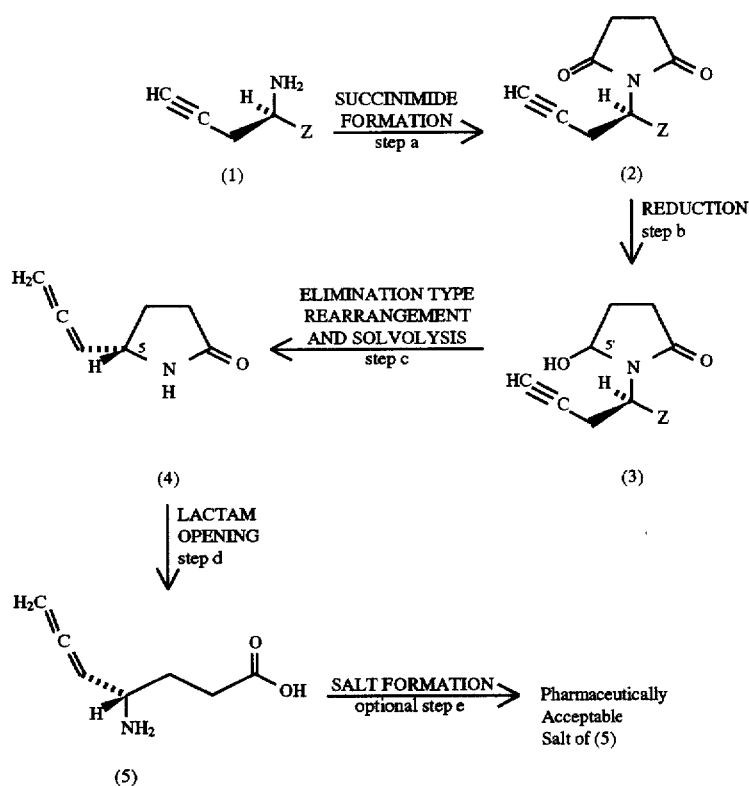

A resolved amine of structure (1) can be obtained by methods well known in the art, such as fractional recrystallization of addition salts formed by reagents used for that purpose, as described in "Enantiomers, Racemates, and Resolutions", J. Jacques, A. Collet, and S. H. Wilen, Wiley (1981) and J. Org. Chem., 50, 4508–4514 (1985), W. ten Hoeve and H. Wynberg.

For example, a racemic amine of the formula:

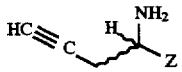

in which Z is as defined above for resolved amine (1) is contacted with an addition salt forming reagent, such as tartaric acid, 10-camphorsulfonic acid, 8-camphorsulfonic acid, 3-bromocamphor-10-sulfonic acid, binaphthylphosphoric acid, 5,5-dimethyl-2-hydroxy-4-(2-methoxyphenyl)-1,3,2-dioxaphosphorinane 2-oxide, 5,5-dimethyl-2-hydroxy-4-(2-ethoxyphenyl)-1,3,2-dioxaphosphorinane 2-oxide, with 5,5-dimethyl-2-hydroxy-4-(2-methoxyphenyl)-1,3,2-dioxaphosphorinane 2-oxide being preferred. The addition salt is formed by warming a mixture of an addition salt forming reagent and a racemic amine in a minimal volume of a suitable solvent, such as ethanol, propanol, isopropanol, or mixtures of alcohols and water. After cooling the precipitated salt is collected by filtration and recrystallized, repeatedly, if needed to increase the enantiomeric purity, from a suitable solvent, such as ethanol, propanol, isopropanol, or mixtures of alcohols and water.

The resolved amine can be recovered as the free amine as is well known in the art by extraction. The free amine can be isolated by evaporation and distillation or by formation of salts which can be recrystallized.

In step a, a resolved amine of structure (1) is contacted with an appropriate succinimide forming reagent to form the succinimide derivative of structure (2).

For example, a resolved amine of structure (1) or a salt of a resolved amine of structure (1) is contacted with an appropriate succinimide forming reagent. Appropriate succinimide forming reagents are well known in the art and include but are not limited to, succinyl chloride, succinic acid, and succinic anhydride, with succinic anhydride being preferred. The reaction maybe optionally carried out in the presence of a suitable base. A suitable base may be utilized to neutralize a salt of the resolved amine or may be utilized to neutralize the acid liberated when the appropriate succinimide forming reagent, such as succinyl chloride, produces acid during the course of the reaction. Suitable bases include but are not limited to, triethylamine, isopropyldiethylamine, pyridine, sodium bicarbonate, and sodium carbonate. The reaction is carried out in a suitable solvent, such as toluene, benzene, or xylene for reactions wherein the appropriate succinimide forming reagent is succinic anhydride or succinic acid and dichloromethane, DMF, THF, or THF/water for reactions wherein the appropriate succinimide forming reagent is succinyl chloride. Succinimide derivatives of structure (2) may be isolated from the reaction zone by extraction and evaporation, as is well known in the art. Succinimide derivatives of structure (2) may be purified by techniques well known in the art, such as chromatography and recrystallization.

In step b, the succinimide derivative of structure (2) is contacted with an appropriate reducing agent to give 5'-hydroxybutyrolactam derivative off structure (3).

As is well known and appreciated in the art, this reduction will give a 5'-hydroxybutyrolactam derivative of structure (3) that is a mixture of stereoisomers at the 5'-position.

Appropriate reducing agents are well known in the art and include but are not limited to lithium tri-t-sec-butoxyaluminohydride, potassium borohydride, lithium tri-sec-butylborohydride, lithium borohydride, sodium borohydride, ant lithium triethylborohydride with sodium borohydride and lithium triethylborohydride being preferred and lithium triethylborohydride being most preferred.

For example, the succinimide derivative of structure (2) is contacted with a molar excess of an appropriate reducing agent. The reaction is carried out in a suitable solvent. Suitable solvents for hydride reductions are well known in the art, such as toluene, diethyl ether, methyl t-butyl ether, and tetrahydrofuran (THF). The reaction is carried out at a temperature that does not allow for over reduction of the imide function but allows the reaction to proceed at a rate that is convenient, such as −78° C. The 5'-hydroxybutyrolactam derivative of structure (3) may be isolated from the reaction zone by extraction and then purifying by methods well known in the art, such as chromatography and recrystallization to give a 5'-hydroxybutyrolactam derivative of the structure (3).

In step c, the 5'-hydroxybutyrolactam derivative of structure (3) is contacted sequentially with an appropriate hydroxyl eliminating acid an appropriate solvolysis agent to give (S)-5-propadienylbutyrolactam (4).

As is well known in the art an appropriate hydroxyl eliminating acid is a protic acid, such as hydrochloric acid, hydrobromic acid, sulfuric acid, phosphoric acid, trifluoroacetic acid, formic acid, trifluoromethanesulfonic acid, methanesulfonic acid, and p-toluenesulfonic acid with trifluoroacetic acid, and with formic acid being preferred and trifluoroacetic acid being most preferred.

The art suggests that this reaction proceeds through theoretical intermediates (a) and (b) as depicted in Scheme Al; [H. Ent et al, Tet. Lets., 24, 2109–2112, (1983); A. L. Castelhano and A. Krantz, J. Am. Chem. Soc., 106, 1877–1879, (1984); Synthesis, 71–82, (1989)].

For example, the 5'-hydroxybutyrolactam derivative of structure (3) is contacted with an appropriate hydroxyl eliminating acid, such as trifluoroacetic acid. The reaction is carried out in a suitable solvent, such as dichloromethane, chloroform, carbon tetrachloride, diethyl ether, methyl t-butyl ether, and tetrahydrofuran. The reaction is carried out at a temperature of from 0° C. to the reflux temperature, and is allowed to stir for from 1–48 hours. The reaction mixture is then contacted with an appropriate solvolysis agent as is well known in the art, such as methanol, ethanol, or water with water being preferred. The (S)-5-propadienylbutyrolactam (4) is isolated from the reaction zone by techniques well known in the art, such as extraction and evaporation and purified by techniques well known in the art, such as chromatography and recrystallization to give (S)-5-propadienylbutyrolactam (4).

In step d, the (S)-5-propadienylbutyrolactam (4) is treated with an appropriate lactam opening reagent to give (S)-4-amino-hepta-5,6-dienoic acid (5).

Appropriate lactam opening reagents can include but are not limited to an aqueous solution of hydrochloric acid or hydrobromic acid, or an aqueous solution of potassium hydroxide, with an aqueous solution of hydrochloric acid being preferred.

For example, (S)-5-propadienylbutyrolactam (4) is contacted with an aqueous 1M hydrochloric acid solution at a temperature of from 20° C. to the refluxing temperature for from 18 hours to 10 days. (S)-4-Amino-hepta-5,6-dienoic acid (5) is purified by methods well known on the art, such as adjusting the pH of the reaction mixture to 5 followed by ion exchange chromatography and recrystallization to give (S)-4-amino-hepta-5,6-dienoic acid.

Alternately, (S)-5-propadienylbutyrolactam (4) is contacted with a molar excess of potassium hydroxide in water. Typically, from about 1.05 to 1.5 equivalents are used. The reaction is carried out in a solvent, such as water or water containing a lower alkanol, such as methanol, ethanol, 1-propanol, 2-propanol, 1-butanol, or 2-butanol with 2-propanol being preferred. The relative proportions of water and lower alkanol can vary widely and are not

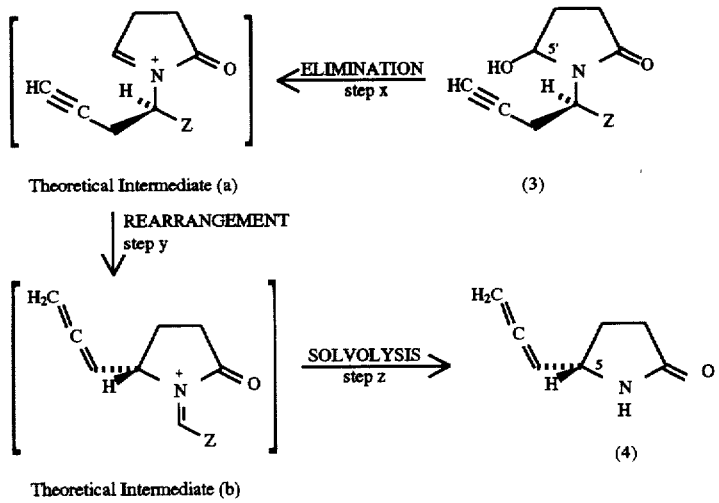

Scheme A1

Theoretical Intermediate (a)  (3)

Theoretical Intermediate (b)  (4)

It is intended that the present invention not be limited by the depiction of or the proposal in the art of these theoretical intermediates.

important for the hydrolysis. The reaction is carried out at a temperature of from 60° C. to refluxing temperature for from 1 hour to 24 hours. (S)-4-Amino-hepta-5,6-dienoic acid (5)

is recovered from the reaction zone by adjusting, if need be, the proportion lower alkanol in the reaction medium. The reaction medium should contain from 60% v/v to about 90% v/v of lower alkanol with 85% being preferred. The mixture is then acidifying with an appropriate acid, such as acetic acid or propanoic acid. The precipitated (S)-4-amino-hepta-5,6-dienoic acid (5) is recovered by filtration.

In optional step e, (S)-4-amino-hepta-5,6-dienoic acid is contacted, as is well known In the art, with a pharmaceutically acceptable acid to form a pharmaceutically acceptable acid addition salt or with a pharmaceutically acceptable base to form a pharmaceutically acceptable base addition salt.

The following examples present typical syntheses as described in Scheme A. These examples are understood to be illustrative only and are not intended to limit the scope of the invention in any way. As used in the following examples, the following terms have the meanings indicated: "g" refers to grams, "mg" refers to milligrams, "mmol" refers to millimoles, "mL" refers to milliliters, "°C." refers to degrees Celsius, "$R_f$" refers to retention factor, "mp" refers to melting point, "dec" refers to decomposition, "$[\alpha]^{20}_D$" refer to specific rotation of the D line of sodium at 20° C. obtained in a 1 decimeter cell, "c" refers to concentration in g/mL, "M" refers to molar, "MeOH" refers to methanol, "2-PrOH" refers to isopropanol, and "TLC" refers to thin layer chromatography.

EXAMPLE 1
(R)-1-Amino-1-phenyl-but-3-yne hydrochloride salt

Dissolve (RS)-1-amino-1-phenyl-but-3-yne [Zh. Org. Khim. 18(4), 980–983 (1982) A. Mostamandi, L. A. Remizova, A. L. Pavienkova, I. A. Favorskayal] (20.0 g, 138 mmol) and (-)-5,5-dimethyl-2-hydroxy-4-(2-methoxyphenyl)-1,3,2,-dioxaphosphorinane 2-oxide (35.0 g, 129 mmol) in refluxing ethanol (300 mL). Cool the solution to ambient temperature and collect the precipitate by filtration. Rinse the precipitate with a small amount of isopropanol/ethanol (1/1). Two recrystallizations from ethanol gives (R)-1-amino-1-phenyl-but-3-yne 5,5-dimethyl-2-hydroxy-4-(2-methoxyphenyl)-1,3,2-dioxaphosphorinane 2-oxide salt (21 g). Combine (R)-1-amino-1-phenyl-but-3-yne 5,5-dimethyl-2-hydroxy-4-(2-methoxyphenyl)-1,3,2-dioxaphosphorinane 2-oxide salt (21 g, 50.4 mmol) with a mixture of aqueous 1M potassium hydroxide solution (100 mL) and toluene (50 mL) and stir or 0.75 hour. Separate the layers and extract the aqueous layer with toluene (50 mL), combine the organic layers, dry over ($Na_2SO_4$), and filter to obtain a solution. Pass hydrogen chloride gas through the solution until it is saturated and then remove the precipitate by filtration and rinse with toluene. Recrystallize from butanone (120 mL) to give 7.0 g the title compound. Specific rotation $[\alpha]^2_D{}^0 = 11.0°$ (c=0.500, MeOH).

EXAMPLE 2
(R)-N-(1-Phenyl-but-3-yne)succinimide

Combine (R)-1-amino-1-phenyl-but-3-yne hydrochloride salt (4.0 g, 22.1 mmol), succinic anhydride (4.4 g, 44.2 mmol) and triethylamine (3.1 mL, 22.1 mmol) in toluene (200 mL) and reflux for 1 hour. Cool to ambient temperature and add triethylamine (3.1 mL, 2.2 g, 22.1 mmol) and then reflux for 18 hours. Cool to ambient temperature and pour into water (200 mL) separate the layers and extract the aqueous layer with ethyl acetate. Combine the combined organic layers and dry ($MgSO_4$). Concentrate the combined organic layers in vacuo to afford crude (R)-N-(1-Phenyl-but-3-yne)succinimide. Purify by flash chromatography (35% ethyl acetate/heptane) combine the product containing fractions and concentrate. Recrystallize (2-PrOH/heptane) to give 4.02 g of the title compound: mp; 109° C. $R_f$=0.23, silica gel TLC, 35% ethyl acetate./heptane. Specific rotation $[\alpha]^2_D{}^0 = 20.0°$ (c=1.000, MeOH). Elem. anal. calcd. for $C_{14}H_{13}NO_2$: C, 76.99; H, 5.70; N, 6.16. Found: C, 76.84; H, 5.83; N, 5.99.

EXAMPLE 3
(1R,5'R and 1R,5'S)-N-(1-Phenyl-but-3-yne)-5'-hydroxybutyrolactam;

Cool a solution of (R)-N-(1-Phenyl-but-3-yne)succinimide (0.1 g, 0.44 mmol) in THF (2 mL) to −78° C. Add a solution of lithium triethylborohydride (0.66mL, 1M in THF, 0.66 mmol) a such a rate that the temperature does not rise above −65° C. Stir for 1 hour after the addition is complete. Add saturated sodium bicarbonate solution (1 mL) and allow the reaction mixture to warm to ambient temperature. Concentrate in vacuo to give an oil. Dissolve the oil in ethyl acetate (10 mL) and wash with water (10 mL), separate the layers and extract the aqueous layer with ethyl acetate (10 mL). Combine the organic layers and wash with saturated sodium chloride solution, dry ($MgSO_4$) and concentrate in vacuo to give an oil. Purify by flash chromatography (35% ethyl acetate/heptane) combine the product containing fractions and concentrate to give the title compound, as a 7:3 mixture of diastereomers at the 5' position, as an oil which solidifies upon cooling. $R_f$=0.04, silica gel TLC, 35% ethyl acetate/heptane. MS (CI/$CH_4$): M+H=230. Specific rotation $[\alpha]^2_D{}^0 = 23.2°$ (c=2.000, MeOH).

EXAMPLE 4
(S)-5-Propadienylbutyrolactam

Add trifluoroacetic acid (12 mL, 15.6 mmol) dropwise to a solution of (1R,5'R and 1R,5'S)-N-(1-Phenyl-but-3-yne)-5'-hydroxybutyrolactam (1.67 g, 7.29 mmol) in methylene chloride (50 mL) and stir for 2 hours. Treat the reaction mixture with water (10 mL) and separate the layers, wash with saturated sodium chloride solution (10 mL). Dry ($MgSO_4$) the organic layer and concentrate to an oil. Purify by flash chromatography (2% methanol/methylene chloride) combine the product containing fractions and concentrate to give the title compound as a solid. $R_f$=0.29, silica gel TLC, 2% methanol/methylene chloride. Elem. anal. calcd. for $C_7H_9NO$: C, 67.77; H, 7.29;N, 11.29. Found: C, 67.71; H, 7.35; N, 11.03. Specific rotation $[\alpha]^2_D{}^0 = 71.0°$ (c=1.060, MeOH).

EXAMPLE 5
(S)-4-Amino-hepta-5,6-dienoic Acid

Heat (S)-5-Propadienylbutyrolactam (0.11 g, 0.89 mmol) and 1M hydrochloric acid (4 mL) to 90° C. for 18 hours. Cool to ambient temperature and add 1M sodium hydroxide until the pH of the solution is 5. Purify by ion exchange chromatography (Dowex 1×2, 100 mesh, hydroxide form) Apply the mixture to the column and wash the resin with water until the column effluent is neutral. Elute the product with 0.25M acetic acid in water. Combine the product containing fractions and concentrate in vacuo to about 20 mL. Lyophilize to give 0.1 g of the title compound: mp; 135° C. (dec). Specific rotation $[\alpha]^2_D{}^0 = 40.60°$ (c=1.020, MeOH).

EXAMPLE 6
(S)-4-Amino-hepta-5,6-dienoic Acid Combine (S)-5-Propadienylbutyrolactam (10 mmol) and potassium (11 mmol) in water (1.1 mL) and 2propanol (13.2 mL) and heat to reflux. After 12 hours, cool the reaction and slowly add acetic acid (11 mmol). Cool the reaction mixture in an ice bath and filter to give the title compound.

What is claimed is:

1. A resolved compound of the formula

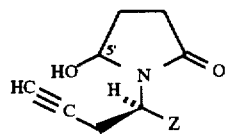

wherein

Z is a phenyl or substituted phenyl bearing from 1 to 3 substituents chosen from the group consisting of $C_1$–$C_4$ alkyl, $C_1$–$C_4$ alkoxy, and halogen.

2. A compound according to claim 1 wherein Z is phenyl.

3. A resolved compound of the formula

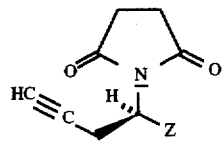

wherein

Z is a phenyl or substituted phenyl bearing from 1 to 3 substituents chosen from the group consisting of $C_1$–$C_4$ alkyl, $C_1$–$C_4$ alkoxy, and halogen.

4. A compound according to claim 3 wherein Z is phenyl.

* * * * *

UNITED STATES PATENT AND TRADEMARK OFFICE
CERTIFICATE OF CORRECTION

PATENT NO. : 5,756,762

DATED : 26 May 1998

INVENTOR(S) :

H. Michael Kolb

It is certified that error appears in the above-indentified patent and that said Letters Patent is hereby corrected as shown below:

Cover Page, Title patent reads: "(S)-4-AMINO-HEPTA-5,6-DIENOIC ACID AND INTERMEIDATES THEROF" and should read --- PROCESSES FOR PREPARING (S) 4-AMINO-HEPTA-5,6-DIENOIC ACID AND INTERMEDIATES THEROF.

Column 1, Line 1 patent reads "(S)-4-amino-hepta-5,6-dienoic acid and intermediates thereof" and should read --- Processes for preparing "(S)-4-amino-hepta-5,6-dienoic acid and intermediates thereof.

Column 1, Line 7 patent reads "1993now" and should read --- 1993, now.

Column 1, Line 11 patent reads "or preparing" and should read --- for preparing.

Column 1, Line 36 patent reads "$C_1$-$C_4$, $C_1$-$C_4$ alkoxy" and should read --- $C_1$-$C_4$ alkyl, $C_1$-$C_4$ alkoxy.

UNITED STATES PATENT AND TRADEMARK OFFICE
CERTIFICATE OF CORRECTION

PATENT NO. : 5,756,762

DATED : 26 May 1998

INVENTOR(S) : H. Michael Kolb

It is certified that error appears in the above-indentified patent and that said Letters Patent is hereby corrected as shown below:

Column 6, Line 17, patent reads "maybe" and should read --- may be.

Column 6, Line 67, patent reads ""off" and should read --- of.

Column 7, Line 5, patent reads "tri-t-sec-butoxy..."And should read --- tri-t-butoxy.

Column 7, Line 8, patent reads "ant" and should read --- and.

Column 8, Line 27, patent reads "for from" and should read --- from.

Column 8, Line 29, patent reads "on the art" and should read --- in the art.

Column 8, Line 66, patent reads "for from" and should read --- from.

Column 9, Line 9, patent reads "In" and should read --- in.

UNITED STATES PATENT AND TRADEMARK OFFICE
CERTIFICATE OF CORRECTION

PATENT NO. : 5,756,762

DATED : 26 May 1998

INVENTOR(S) : H. Michael Kolb

It is certified that error appears in the above-indentified patent and that said Letters Patent is hereby corrected as shown below:

Column 10, Line 13, patent reads "a such a" and should read --- at such a.

Column 10, Line 62, patent reads "Acid Comine" and should read --- Acid. {new paragraph} Combine.

Column 10, Line 64, patent reads "2propanol" and should read --- 2-propanol.

Signed and Sealed this

Second Day of November, 1999

Attest:

Attesting Officer

Q. TODD DICKINSON

Acting Commissioner of Patents and Trademarks